United States Patent [19]

Watanabe et al.

[11] Patent Number: 5,310,620
[45] Date of Patent: May 10, 1994

[54] ALKALI-SOLUBLE NITRONE COMPOUNDS AND CONTRAST ENHANCED MATERIAL COMPRISING THE SAME

[75] Inventors: Satoshi Watanabe; Toshinobu Ishihara; Ken'Ichi Itoh, all of Jouetsu, Japan

[73] Assignee: Shin-Etsu Chemical Co., Ltd., Tokyo, Japan

[21] Appl. No.: 971,650

[22] Filed: Nov. 5, 1992

[30] Foreign Application Priority Data

Dec. 6, 1991 [JP] Japan .................. 3-348992
Jan. 30, 1992 [JP] Japan .................. 4-040424

[51] Int. Cl.$^5$ .................. C07C 251/24; C07C 251/16; G03C 1/00
[52] U.S. Cl. .................. 430/272; 430/273; 430/312; 562/440
[58] Field of Search .......... 562/440; 430/272, 273, 430/312

[56] References Cited

U.S. PATENT DOCUMENTS

| | | | |
|---|---|---|---|
| 4,677,049 | 6/1987 | Griffing et al. | 430/339 |
| 4,702,996 | 10/1987 | Griffing et al. | 430/325 |
| 4,822,716 | 4/1989 | Onishi et al. | 430/192 |
| 4,859,789 | 8/1989 | Griffing et al. | 560/35 |
| 4,990,665 | 2/1991 | Griffing et al. | 564/265 |
| 5,108,874 | 4/1992 | Griffing et al. | 430/273 |

FOREIGN PATENT DOCUMENTS 37-40697 8/1962 Japan .
62-234148 10/1987 Japan .

*Primary Examiner*—Allen J. Robinson
*Assistant Examiner*—P. O'Sullivan
*Attorney, Agent, or Firm*—Millen, White, Zelano & Branigan

[57] ABSTRACT

Novel nitrone compounds of the following formula are provided

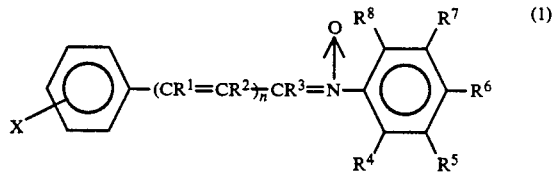

wherein $R^1$, $R^2$ and $R^3$ may be the same or different and represent an alkyl group, an aryl group or a hydrogen atom, $R^4$ to $R^8$ may be the same or different and represent an alkyl group, a hydrogen atom or a carboxyl group provided that at least one of $R^4$ to $R^8$ is a carboxyl group, X represents an alkoxy group of the formula, $R^9O$—, wherein $R^9$ represents an alkyl group, a dialkylamino group of the formula, $R^{10}R^{11}N$—, wherein $R^{10}$ and $R^{11}$ may be the same or different and represent an alkyl group, or a hydrogen atom, and n is a value of 0, 1 or 2. A contrast enhanced material comprising the nitrone compound is also provided, which is able to enhance a contrast when exposed to light having a wavelength of 300 to 450 nm.

19 Claims, 2 Drawing Sheets

ALKALI-SOLUBLE NITRONE COMPOUNDS AND CONTRAST ENHANCED MATERIAL COMPRISING THE SAME

BACKGROUND OF THE INVENTION

1. Field of the Invention

This invention relates to novel nitrone compounds which are suitable for use as a main ingredient of a contrast enhanced material for enhancing an image contrast of a subject, like a mask for photoetching used for fabrication, for example, of semiconductive integrated circuits and also to contrast enhanced materials which comprises the nitrone compounds.

2. Description of the Prior Art

In lithographic techniques, a resist image which is obtained by exposing a photo-resist to light in a desired pattern and developing the pattern has more vertically shaped walls when the contrast of the exposed image is greater. When the exposure is carried out at a very high resolution, the contrast of the exposed image is lowered with the attendant problem that a clear resist image cannot be obtained.

For increasing the resolution and obtaining a high resolution pattern, there have been proposed methods of forming resist patterns wherein a contrast enhanced layer for enhancing the contrast which has an absorption maximum against light having a wavelength of 300 to 450 nm (Japanese Patent Publication No. 62-40697 and Japanese Laid-Open Patent Application No. 62-234148). The nitrone compounds used as a main ingredient for the contrast enhanced material have the following structures.

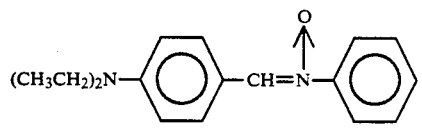

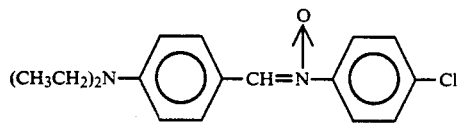

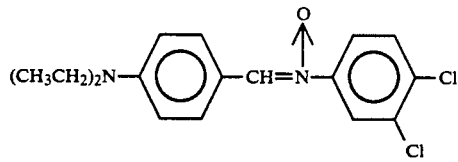

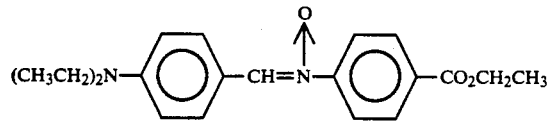

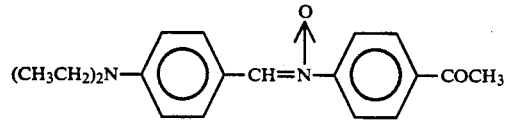

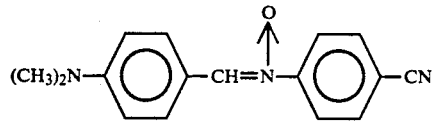

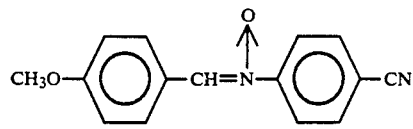

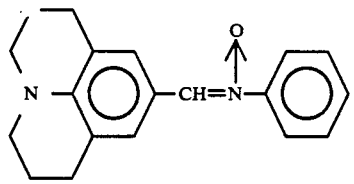

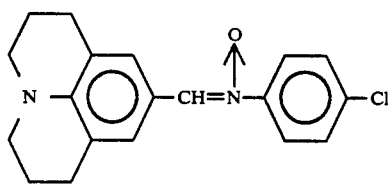

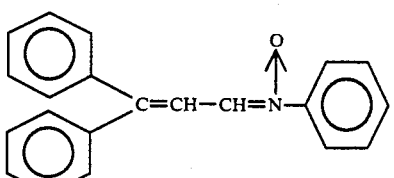

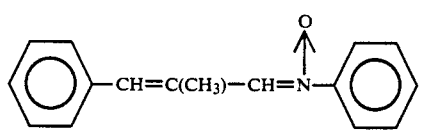

However, the above-mentioned nitrone compounds are insoluble in water and are soluble only in organic solvents. Accordingly, the contrast enhanced materials using the nitrone compounds cannot be soluble in water. This requires the step of removing the contrast enhanced layer with use of organic solvents prior to the developing step of a photoresist. Alternatively, if an intervening layer is provided, it is essentially required to force the intervening layer and the contrast enhanced layer to be blown off by means of pure water. The former removing step using the organic solvent cannot be performed in existing apparatus, inviting complication of the fabrication procedure. With the latter procedure wherein pure water is used to blow the layer off along with the intervening layer, there is the problem that the contrast enhanced layer cannot be completely blown off but is partly left, thus producing scums. Accordingly, there is the demand for nitrone compounds which are useful as an ingredient for contrast enhanced materials and which do not invite complication of the steps and are soluble in pure water.

SUMMARY OF THE INVENTION

It is accordingly an object of the invention to provide novel alkali-soluble nitrone compounds which are soluble in pure water and which are useful as a main ingredient of contrast enhanced materials.

It is another object of the invention to provide a contrast enhanced material which comprises the novel nitrone compound.

The above objects can be achieved, according to one embodiment of the invention, by a novel alkali-soluble nitrone compound of the following formula

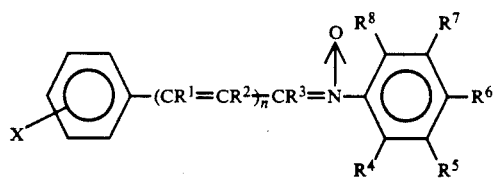

wherein $R^1$, $R^2$ and $R^3$ may be the same or different and represent an alkyl group, an aryl group or a hydrogen atom, $R^4$ to $R^8$ may be the same or different and represent an alkyl group, a hydrogen atom or a carboxyl group provided that at least one of $R^4$ to $R^8$ is a carboxyl group, X represents an alkoxy group of the formula, $R^9O—$, wherein $R^9$ represents an alkyl group, a dialkylamino group of the formula, $R^{10}R^{11}N—$, wherein $R^{10}$ and $R^{11}$ may be the same or different and represent an alkyl group, or a hydrogen atom, and n is a value of 0, 1 or 2.

The novel nitrone compound can be obtained, for example, by subjecting an alkylnitrobenzoic acid of the following formula (2) to hydrogenation, followed by reaction with a compound of the general formula (3) to obtain novel, alkali-soluble nitrone compounds of the following formula (1)

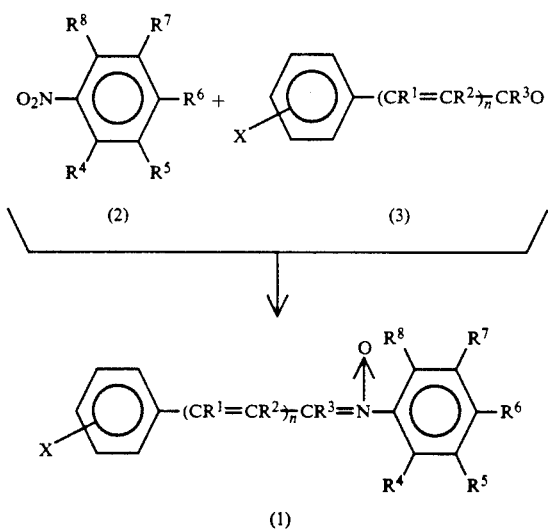

wherein $R^1$ to $R^8$ have, respectively, the same meanings as defined above.

The novel nitrone compounds have been found to be useful as an main ingredient for contrast enhanced materials and have shown great effects in the contrast enhanced lithography using light having a wavelength of from 300 to 450 nm.

More particularly, the novel nitrone compounds of the formula (1) is alkali-soluble and has contrast enhancing properties against light having a wavelength of from 300 to 450 nm. Thus, it is possible to provide a water-soluble contrast enhanced material which has never been expected using existing nitrone compounds. This means that a contrast enhanced layer may be removed not only with organic solvents, but also with water. Existing apparatus may be used as it is without causing the steps to be complicated and without formation of any scum when using an intervening layer. Accordingly, when the nitrone compound of the formula (1) is used to prepare a contrast enhanced material for carrying out the contrast enhanced lithography at g line (light with a wavelength of 436 nm) of an i line (light with a wavelength of 365 nm), there can be formed a fine resist pattern which has high contrast, high resolution and high precision.

According to another embodiment of the invention, there is also provided a contrast enhanced material which comprises a nitrone compound of the formula (1).

DETAILED DESCRIPTION AND EMBODIMENTS OF THE INVENTION

Figure 1A:
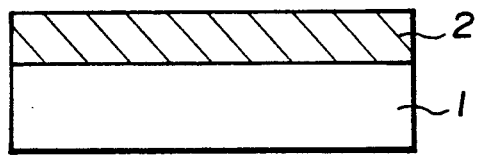
FIGS. 1(a) to 1(d) are a flow sheet showing a series of lithographic steps using a contrast enhanced material according to one embodiment of the invention.

As stated before, the novel nitrone compound of the invention has the following general formula (1).

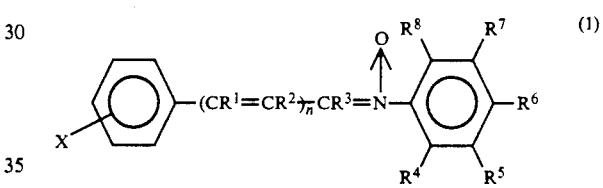

In the above formula, $R^1$, $R^2$ and $R^3$ are independently an alkyl group, an aryl group or a hydrogen atom. Examples of the alkyl group are those having from 1 to 8 carbon atoms, including a methyl group, an ethyl group, a propyl group, an iso-propyl group, a butyl group, a sec-butyl group, a tert-butyl group, a cyclohexyl group and the like. Of these, there are preferred a methyl group, an ethyl group, a propyl group and a butyl group. The aryl groups are those having from 6 to 15 carbon atoms and include, for example, a phenyl group, substituted phenyl groups, a naphthyl group, substituted naphthyl groups and the like. Of these, a phenyl group, a methylphenyl group, and an ethylphenyl group are preferred. $R^4$, $R^5$, $R^6$, $R^7$ and $R^8$ may be the same or different and represent an alkyl group or a hydrogen atom or a carboxyl group provided that at least one of $R^4$, $R^5$, $R^6$, $R^7$ and $R^8$ a carboxyl group. The alkyl group in this case may be those indicated with respect to $R^1$, $R^2$ and $R^3$. X represents an alkoxy group of the formula, $R^9O—$, wherein $R^9$ represents an alkyl group, a dialkylamino group of the formula, $R^{10}R^{11}N—$, wherein $R^{10}$ and $R^{11}$ may be the same or different and represent an alkyl group, or a hydrogen atom. The alkyl group for $R^9$, $R^{10}$ and $R^{11}$ is one represented by $R^{11}$, $R^2$ and $R^3$. Letter n is a value of 0, 1 or 2, preferably 0 or 1.

More specific examples of the nitrone compound of the formula (1) include those of the following formulae.

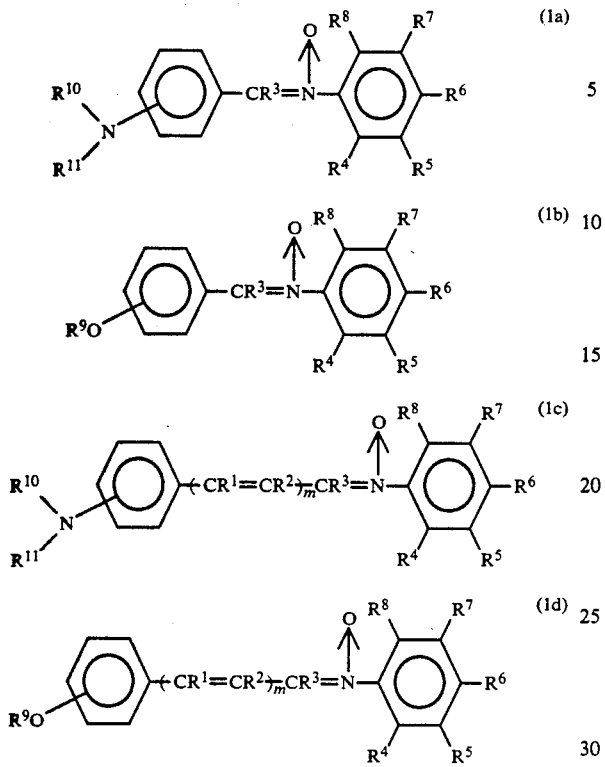

(wherein m=1 or 2)

Specific examples of the nitrone compounds of the formula (1) include α-[p-(dimethylamino)phenyl]-N-(4-carboxyphenyl)nitrone, α-[p-(diethylamino)phenyl]-N-(4-carboxyphenyl)nitrone, α-[p-(dibutylamino)phenyl]-N-(4-carboxyphenyl)nitrone, α-[p-(diethylamino)phenyl]-N-(3-carboxyphenyl)nitrone, α-[p-(diethylamino)phenyl]-N-(2-carboxyphenyl)nitrone, α-[p-(diethylamino)phenyl]-N-(2-methyl-4-carboxyphenyl)nitrone, α-[p-(diethylamino)phenyl]-N-(2-methyl-3-carboxyphenyl)nitrone, α-(p-methoxyphenyl)-N-(4-carboxyphenyl)nitrone, α-(p-ethoxyphenyl)-N-(4-carboxyphenyl)nitrone, α-(o-methoxyphenyl)-N-(4-carboxyphenyl)nitrone, α-(p-methoxyphenyl)-N-(3-carboxyphenyl)nitrone, α-(p-methoxyphenyl)-N-(2-carboxyphenyl)nitrone, α-(p-methoxyphenyl)-N-(2-methyl-4-carboxyphenyl)nitrone, α-(p-ethoxyphenyl)-N-(3-methyl-2carboxy-phenyl)nitrone, α-[p-(dimethylamino)styryl]-N-(4-carboxypenyl)nitrone, α-[p-(diethylamino)styryl]-N-(4-carboxyphenyl)nitrone, α-[p-(dimethylamino)styryl]-N-(3-carboxyphenyl)nitrone, α-[p-(diethylamino)styryl]-N-(2-methyl-4-carboxypheyl)nitrone, α-[p-(diethylamino)styryl]-N-(4-methyl-2-carboxyphenyl)nitrone, α-(o-methoxystyryl)-N-(4-carboxyphenyl)nitrone, α-(o-methoxystyryl)-N-(3-carboxyphenyl)nitrone, α-(p-methoxystyryl)-N-(4-carboxyphenyl)nitrone, α-(p-methoxystyryl)-N-(3-carboxyphenyl)nitrone, α-(o-methoxystyryl)-N-(2-methyl-4-carboxyphenyl)nitrone, α-(p-methoxystyryl)-N-(2-methyl-3-carboxyphenyl)nitrone and the like.

The nitrone compounds of the formula (1) of the invention can be prepared by providing, as a starting material, an alkylnitrobenzoic acid of the following formula (2) which are readily available on an industrial scale, subjecting the alkylnitrobenzoic acid of the formula (2) to hydrogenation reaction according to the following reaction sequence to obtain a compound of the following general formula (4), and subjecting to further reaction with a compound of the general compound (3).

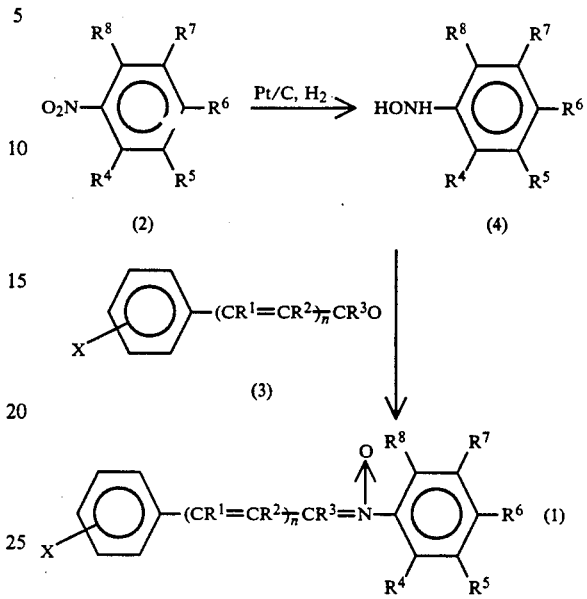

The above reaction should preferably be carried out in organic solvents such as methanol. The hydrogenation of the alkylnitrobenzoic acid of the formula (2) is performed at room temperature in the presence of a catalytic amount of a catalyst such as a platinum-on-carbon catalyst in such a way that 1.7 to 2.3 equivalents of hydrogen relative to the alkylnitrobenzoic acid are filled at a pressure of from 1 to 10 kg/cm².

For the reaction between the hydrogenated alkylnitrobenzoic acid and the compound of the formula (3), it is preferred that the compound of the formula (3) is added in amounts of from 0.8 to 1.2 moles per mole of the alkylnitrobenzoic acid and the reaction is effected in the presence of an acid such as acetic acid. The reaction conditions should preferably include a temperature of from 20° to 50° C. and a time of from 3 to 8 hours. After completion of the reaction, the precipitated crystals are removed by filtration and washed with appropriate solvents to obtain an intended nitrone compound of the formula (1).

The contrast enhanced material of the invention should comprise the nitrone compound of the formula (1). The nitrone compound may be dissolved in water or organic solvents along with binders, organic bases, surface active agents and the like to provide a rotational casting contrast enhanced material. The contrast enhanced material should preferably comprise (A) from 0 to 100 parts by weight (hereinafter referred to simply as parts), preferably from 50 to 100 parts, of water, (B) from 0 to 100 parts, preferably from 0 to 50 parts, of an organic solvent, (C) from 1 to 30 parts, preferably from 1 to 15 parts, of a water-soluble polymer binder, (D) from 1 to 30 parts, preferably from 1 to 15 parts, of the nitrone compound, (E) from 1 to 30 parts, preferably from 1 to 15 parts, of an organic base, and (F) from 0 to 2 parts, preferably from 0 to 1 part, of a surface active agent. As will be apparent from the above, the contrast enhanced material should essentially contain the ingredients (C), (D) and (E).

The organic solvents used as the (B) ingredient include, for example, alcohols such as ethanol, 1-propanol, 2-propanol and the like, and ethers such as tetrahydrofuran, 1,4-dioxane and the like.

The binders used as the (C) ingredient include, for example, partially saponified products of vinyl acetate polymers, polyvinyl alcohol, water-soluble cellulose ethers or cellulose esters, vinyl pyrrolidone homopolymers or copolymers, pullulans and the like.

The organic bases used as the (E) ingredient include, for example, tetramethylammonium hydroxide, tetrabutylammonium hydroxide, tris(hydroxymethyl)aminomethane, 2,2',2"-nitrilotriethanol, pyridine, triethylamine and the like.

The surface active agents used as the (F) ingredient include, for example, fluorine-containing surface active agents.

Figure 1B:
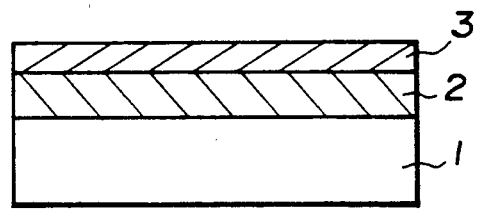
Figure 1C:
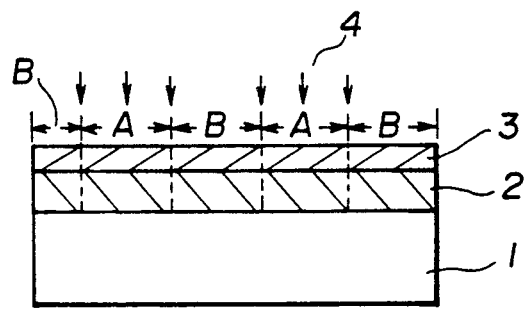
Figure 1D:
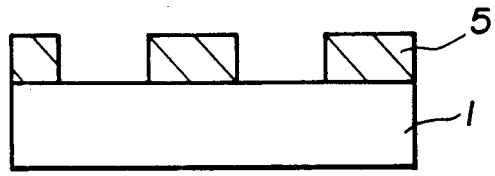
Figure 2A:
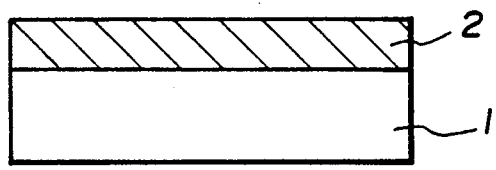
FIGS. 2(a) to 2(e) are a flow sheet showing a series of lithographic steps using a contrast enhanced material according to another embodiment of the invention.
Figure 2B:
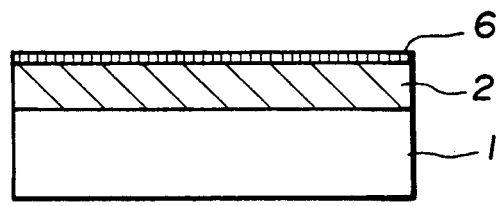
Figure 2C:
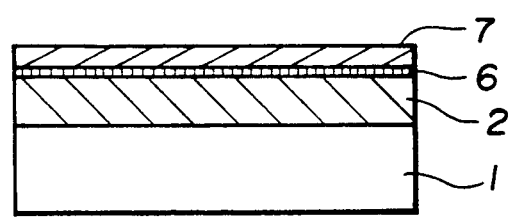
Figure 2D:
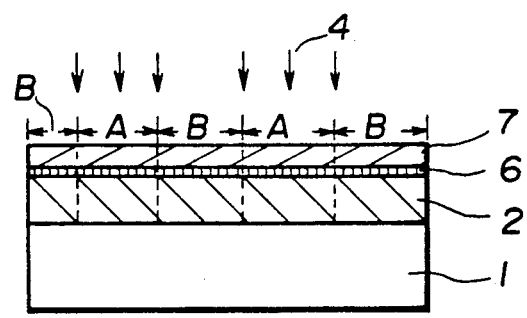
Figure 2E:
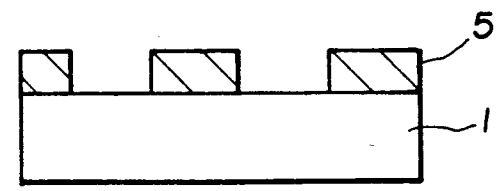

For the formation of a resist pattern from the contrast enhanced material according to the invention, lithographic procedures as shown in FIGS. 1 and 2 are used. FIG. 1 shows an embodiment wherein a contrast enhanced layer is directly formed on a photoresist layer. More particularly, a photoresist layer 2 is formed on a substrate 1, such as a silicon wafer, by a coating technique such as spin coating. Subsequently, a contrast enhanced material of the invention is applied, such as by spin coating, onto the photoresist layer 2 to form a contrast enhanced layer 3. The contrast enhanced layer 3 is exposed to a UV ray with a predetermined wavelength in an imagewise pattern according to a reduced projection method. In FIG. 1, portions A are exposed to the ray, after which the contrast enhanced layer 3 is removed by means of water, followed by developer to form a resist pattern 5.

In FIG. 2, there is shown an embodiment wherein a thin intervening layer 6 made of a neutral material such as polyvinyl alcohol is provided between the contrast enhanced layer and the photoresist layer so that both layers are kept away from each other. In this case, since the contrast enhanced material of the invention is soluble in water, the contrast enhanced layer 3 and the intervening layer 6 are both washed away with water, so that any scum is not produced.

The nitrone compound of the formula (1) of the invention suffers contrast enhancement against g and i lines and is soluble in alkalis or bases, with which there can be provided water-soluble contrast enhanced materials which are capable of forming a fine resist pattern with high contrast, high resolution and high precision. Thus, the nitrone compound is very useful as a main ingredient of a water-soluble contrast enhanced material for contrast improvement by which a fine resist pattern can be formed.

The invention is more particularly described by way of examples, which should not be construed as limiting the invention.

EXAMPLE 1

122.2 g (731 mmols) of p-nitrobenzoic acid, 11.3 g of dimethylsulfoxide, 2.0 g of a 5% platinum-supported catalyst, and 260 g of methanol were charged into a one liter autoclave, followed by filling hydrogen at a pressure of about 4 kg/cm$^2$ and continuing agitation at room temperature until an equivalent of hydrogen was reacted with p-nitrobenzoic acid. After removal of the catalyst, 120.0 g (677 mmols) of 4-diethylaminobenzaldehyde, 30.0 g of acetic acid and 100 g of methanol were added to the resultant residue, followed by agitation at room temperature for 5 hours. After removal of the resultant crystals by filtration, they were washed with methanol to obtain yellow crystals and dried to isolate 187.6 g (yield 88.7%) of α-p-(diethylamino)-phenyl]-N-(4-carboxyphenyl)nitrone with a purity of 96%. The thus obtained α-[p-(diethylamino)-phenyl]-N-(4-carboxyphenyl)nitrone had the following results with respect to mass spectra (MS), NMR spectra (NMR), IR spectra (IR) and elementary analysis.

MS: m/e spectral intensity ratio
312 (16.5), 297 (8.1), 296 (15.1), 281 (24.6), 176 (100.0), 32 (31.5)

$^1$H-NMR: δ(ppm)

$$(CH_3CH_2)_2N\underset{a\ b}{-}\underset{}{\bigcirc}\underset{c\ d}{-}CH\underset{e}{=}\overset{O}{\overset{\uparrow}{N}}\underset{f\ g}{-}\underset{}{\bigcirc}\underset{h}{-}CO_2H$$

| | | | |
|---|---|---|---|
| (a) | 1.2 | triplet | 6H |
| (b), (h) | 3.3-3.8 | multiplet | 5H |
| (c) | 8.4 | doublet | 2H |
| (d) | 6.8 | doublet | 2H |
| (e) | 8.3 | singlet | 1H |
| (f), (g) | 8.8 | singlet | 4H |

IR: (cm$^{-1}$)
3437, 2976, 2900, 1705, 1605, 1572, 1523, 1410, 1275, 1180, 1155, 1122, 1080, 1036, 1011, 879, 860, 817

Elementary analysis: (%) C$_{18}$H$_{20}$N$_2$O$_3$ Calculated C: 69.2; H: 6.4.; N: 9.0; Found C: 68.1; H: 6.2; N: 8.5.

EXAMPLE 2

The general procedure of Example 1 was repeated except that 132.4 g (731 mmols) of 3-methyl-4-nitrobenzoic acid was used instead of p-nitrobenzoic acid, thereby obtaining 211.3 g (yield 95.6%) of α-[p-(diethylamino)phenyl]-N-(2-methyl-4-carboxyphenyl)nitrone with a purity of 95%. The results of the analyses of the thus obtained compound are shown below.

MS: m/e spectral intensity ratio
326 (20.3), 311 (15.3), 310 (6.7), 295 (8.9), 176 (100.0), 32 (26.0)

$^1$H-NMR: δ(ppm)

$$(CH_3CH_2)_2N\underset{a\ b}{-}\underset{}{\bigcirc}\underset{c}{-}CH\underset{c}{=}\overset{O}{\overset{\uparrow}{N}}\underset{c}{-}\underset{\underset{d}{CH_3}}{\bigcirc}\underset{e}{-}CO_2H$$

| | | | |
|---|---|---|---|
| (a) | 1.1 | triplet | 6H |
| (b) | 3.4 | quadruplet | 4H |
| (c) | 6.6-8.3 | multiplet | 8H |
| (d) | 2.4 | singlet | 3H |
| (e) | 3.2 | singlet | 1H |

IR: (cm$^{-1}$)
3435, 3053, 2974, 2902, 1703, 1591, 1524, 1408, 1273, 1176, 1155, 1122, 1078, 1039, 1009, 877, 854, 817

Elementary analysis: (%) C$_{19}$H$_{22}$N$_2$O$_3$; Calculated C: 69.9; H: 6.7; N: 8.6; Found C: 67.4; H: 6.4; N: 8.0.

EXAMPLE 3

The general procedure of Example 1 was repeated except that 92.2 g (677 mmols) of p-anisaldehyde was used instead of 4-diethylaminobenzaldehyde, thereby obtaining 162.0 g (yield 88.2%) of α-(p-methoxyphenyl)-N-(4-carboxyphenyl)nitrone with a purity of 96%. The results of the analyses of the thus obtained compound are shown below.

$^1$H-NMR: δ(ppm)

$$\underset{a}{CH_3O}-\underset{b\ c}{\underset{}{\bigcirc}}-\underset{d}{CH}=\underset{}{\overset{\overset{O}{\uparrow}}{N}}-\underset{e\ f}{\underset{}{\bigcirc}}-\underset{g}{COOH}$$

| | | | |
|---|---|---|---|
| (a) | 3.84 | singlet | 3H |
| (b) | 8.51 | doublet | 2H |
| (c) | 7.07 | doublet | 2H |
| (d) | 8.49 | singlet | 1H |
| (e) | 8.07 | doublet | 2H |
| (f) | 8.08 | doublet | 2H |
| (g) | not detected | | 1H |

IR: (cm$^{-1}$)
3456, 3109, 3157, 2968, 2841, 2673, 2551, 1703, 1686, 1603, 1508, 1431, 1323, 1292, 1251, 1169, 1070, 1028, 870, 841, 806

Elementary analysis: (%) $C_{15}H_{13}NO_4$; Calculated C: 66.4; H: 4.8; N: 5.2; Found C: 66.1; H: 4.9; N: 4.8.

EXAMPLE 4

The general procedure of Example 1 was repeated except that 132.4 g (731 mmols) of 3-methyl-4-nitrobenzoic acid was used instead of p-nitrobenzoic acid and 118.6 g (677 mmols) of 4-dimethylaminocinnamaldehyde was used instead of 4-diethylaminobenzaldehyde, thereby obtaining 213.8 g (yield 97.4%) of α-[p-(dimethylamino)styryl]-N-(2-methyl-4-carboxyphenyl)nitrone with a purity of 96%. The results of the analyses of the thus obtained compound are shown below.

$^1$H-NMR: δ(ppm)

$$\underset{a}{(CH_3)_2N}-\underset{b\ c}{\underset{}{\bigcirc}}-\underset{d}{CH}=\underset{e}{CH}-\underset{f}{CH}=\underset{}{\overset{\overset{O}{\uparrow}}{N}}-\underset{g\ h}{\underset{\underset{CH_3}{|}}{\bigcirc}}\underset{j}{}-\underset{k}{COOH}$$

| | | | |
|---|---|---|---|
| (a) | 3.00 | singlet | 6H |
| (b) | 6.75 | doublet | 2H |
| (c) | 7.47 | doublet | 2H |
| (d) | 7.26 | singlet | 1H |
| (e) | 7.27 | doublet | 1H |
| (f) | 7.78 | doublet | 1H |
| (g) | 7.89 | doublet | 1H |
| (h) | 7.50 | doublet | 1H |
| (i) | 7.94 | singlet | 1H |
| (j) | 2.40 | singlet | 3H |
| (k) | not detected | | 1H |

IR: (cm$^{-1}$)
3446, 3037, 2891, 2812, 1701, 1593, 1524, 1487, 1435, 1367, 1329, 1275, 1234, 1232, 1165, 1126, 1105, 1018, 984, 945, 924, 920, 860, 841, 810

Elementary analysis: (%) $C_{19}H_{20}N_3O_2$; Calculated C: 70.4; H: 6.2; N: 8.6; Found C: 69.9; H: 6.3; N: 8.4.

EXAMPLE 5

As a contrast enhanced material, there was provided an aqueous solution which contained 4.5% of α-[p-(diethylaminophenyl]-N-(4-carboxyphenyl)nitrone, 3.5% of a vinyl pyrrolidone-vinyl acetate copolymer having a molecular weight of about 3,000 and a monomer ratio of 6:4, 38.0% of a 10% tetra-n-butylammonium hydroxide solution, and 0.25% of Florad FC-430 (available from Sumitomo 3M Co., Ltd.) to form a resist pattern according to the lithographic process shown in FIG. 1. More particularly, S-1813 (positive resist, available from Shipray Co., Ltd.) was spin coated on a substrate 1 made of a silicon wafer to form a resist layer 2 (FIG. 1(a)). Then, the contrast enhanced material indicated above was spin coated onto the resist layer 2 to form a contrast enhanced layer 3 (FIG. 1(b)). Thereafter, a UV ray 4 having a wavelength of 436 nm was selectively exposed on portions A according to a reduced projection method (FIG. 1(c)). Finally, the contrast enhanced layer 3 was removed with use of pure water, followed by development with an alkaline developer to form a resist pattern 5. (FIG. 1(d)). The thus obtained resist pattern was enhanced in contrast with a resolution of 0.5 μm.

EXAMPLE 6

There was provided, as a contrast enhanced material, an aqueous solution which contained 4.5 % of α-[p-(diethylaminophenyl-N-(2-methyl-4-carboxyphenyl)nitrone, 3.5% of a vinyl pyrrolidone-vinyl acetate copolymer having a molecular weight of about 3000 and a monomer ratio of 6:4, 2.0% of tris(hydroxymethyl)aminomethane, and 0.25% of Florad FC-430 (available from Sumitomo 3M Co., Ltd.) to form a resist pattern according to the lithographic process shown in FIG. 1. More particularly, THMR-iP1800 (positive resist, available from Tokyo Applied Chem. Ind. Co., Ltd.) was spin coated on a substrate 1 made of a silicon wafer to form a resist layer 2 (FIG. 1(a)). Then, the contrast enhanced material indicated above was spin coated onto the resist layer 2 to form a contrast enhanced layer 3 (FIG. 1(b)). Thereafter, a UV ray 4 having a wavelength of 365 nm was selectively exposed on portions A according to a reduced projection method (FIG. 1(c)). Finally, the contrast enhanced layer 3 was removed with use of pure water, followed by development with an alkaline developer to form a resist pattern 5 (FIG. 1(d)). The thus obtained resist pattern was enhanced in contrast with a resolution of 0.36 μm.

EXAMPLE 7

The general procedure of Example 6 was repeated except that there was used α-(p-methoxyphenyl)-N-(4-carboxyphenyl)nitrone instead of α-[p-(diethylaminophenyl)-N-(2-methyl-4-carboxyphenyl)nitrone, thereby forming a resist pattern whose contrast was enhanced with a resolution of 0.4 μm.

EXAMPLE 8

The general procedure of Example 5 was repeated except that there was used a pure water-1-propanol solution (ratio by weight of 65:35) which contained 4.5% of α-[p-dimethylamino)styryl]-N-(2-methyl-4-carboxyphenyl)nitrone, 3.5% of vinyl pyrrolidone-vinyl acetate copolymer having a molecular weight of about 3,000 and a monomer ratio by weight of 6:4, 2% of tris(hydroxymethyl)aminomethane, and 0.25% of Floprad FC-430 (available from Sumitomo 3M Co., Ltd.), thereby forming a resist pattern. The pattern was enhanced in contrast with a resolution of 0.5 μm.

What is claimed is:

1. An alkali-soluble nitrone compound of the following formula

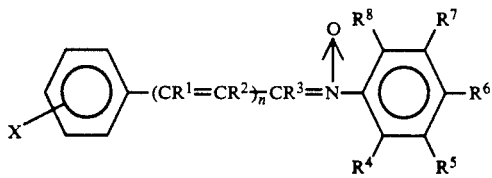

(1)

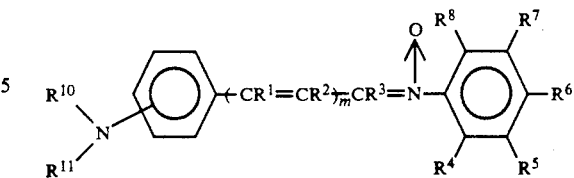

wherein $R^1$, $R^2$ and $R^3$ may be the same or different and represent an alkyl group, an aryl group or a hydrogen atom, $R^4$ to $R^8$ may be the same or different and represent an alkyl group, a hydrogen atom or a carboxyl group provided that at least one of $R^4$ to $R^8$ is a carboxyl group, X represents an alkoxy group of the formula, $R^9O-$, wherein $R^9$ represents an alkyl group, a dialkylamino group of the formula, $R^{10}R^{11}N-$, wherein $R^{10}$ and $R^{11}$ may be the same or different and represent an alkyl group, or a hydrogen atom, and n is a value of 0, 1 or 2.

2. An alkali-soluble nitrone compound according to claim 1, wherein $R^1$, $R^2$ and $R^3$ are independently an alkyl group having from 1 to 8 carbon atoms.

3. An alkali-soluble nitrone compound according to claim 1, wherein $R^1$, $R^2$ and $R^3$ are independently an aryl group having from 6 to 15 carbon atoms.

4. An alkali-soluble nitrone compound according to claim 1, wherein n is 0 or 1.

5. An alkali-soluble nitrone compound according to claim 1, wherein said nitrone compound is of the formula

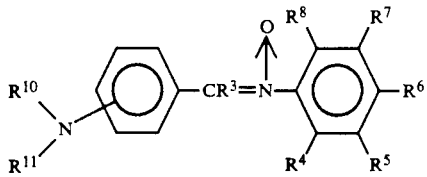

wherein $R^3$, $R^4$, $R^5$, $R^6$, $R^7$, $R^8$, $R^{10}$ and $R^{11}$ have, respectively, the same meanings as defined in claim 1.

6. An alkali-soluble nitrone compound according to claim 1, wherein said nitrone compound is of the formula

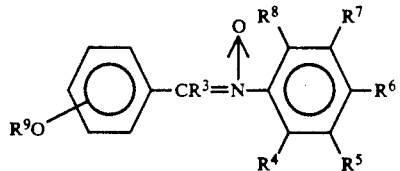

wherein $R^3$, $R^4$, $R^5$, $R^6$, $R^7$, $R^8$, $R^9$ have, respectively, the same meanings as defined in claim 1.

7. An alkali-soluble nitrone compound according to claim 1, wherein said nitrone compound is of the formula wherein $R^1$, $R^2$, $R^3$, $R^4$, $R^5$, $R^6$, $R^7$, $R^8$ $R^{10}$ and $R^{11}$ have, respectively, the same meanings as defined in claim 1 and m is 1 or 2.

8. An alkali-soluble nitrone compound according to claim 1, wherein said nitrone compound is of the formula

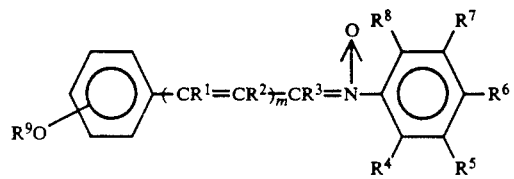

wherein $R^1$, $R^2$, $R^3$, $R^4$, $R^5$, $R^6$, $R^7$, $R^8$, and $R^9$ have, respectively, the same meanings as defined in claim 1 and m is 1 or 2.

9. A contrast enhanced material which comprises an alkali-soluble nitrone compound of the following formula

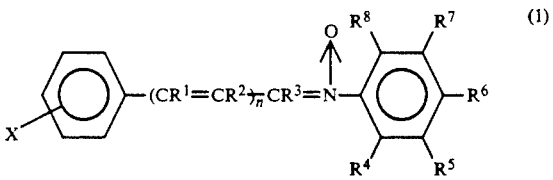

(1)

wherein $R^1$, $R^2$ and $R^3$ may be the same or different and represent an alkyl group, an aryl group or a hydrogen atom, $R^4$ to $R^8$ may be the same or different and represent an alkyl group, a hydrogen atom or a carboxyl group provided that at least one of $R^4$ to $R^8$ is a carboxyl group, X represents an alkoxy group of the formula, $R^9O-$, wherein $R^9$ represents an alkyl group, a dialkylamino group of the formula, $R^{10}R^{11}N-$, wherein $R^{10}$ and $R^{11}$ may be the same or different and represent an alkyl group, or a hydrogen atom, and n is a value of 0, 1 or 2.

10. A contrast enhanced material according to claim 9, which comprises from 0 to 100 parts by weight of water, from 0 to 100 parts by weight of an organic solvent, from 1 to 30 parts by weight of a water-soluble polymer binder, from 1 to 30 parts by weight of said nitrone compound, from 1 to 30 parts by weight of an organic base, and from 0 to 2 parts by weight of a surface active agent.

11. A contrast enhanced material according to claim 10, which comprises from 50 to 100 parts by weight of water, from 0 to 50 parts by weight of an organic solvent, from 1 to 15 parts by weight of a water-soluble polymer binder, from 1 to 15 parts by weight of said nitrone compound, from 1 to 15 parts by weight of an organic base, and from 0 to 1 part by weight of a surface active agent.

12. A contrast enhanced material according to claim 9, wherein $R^1$, $R^2$ and $R^3$ are independently an alkyl group having from 1 to 8 carbon atoms.

13. A contrast enhanced material according to claim 9, wherein $R^1$, $R^2$ and $R^3$ are independently an aryl group having from 6 to 15 atoms.

14. A contrast enhanced material according to claim 9, wherein n is 0 or 1.

15. A contrast enhanced material according to claim 9, wherein said material is of the formula

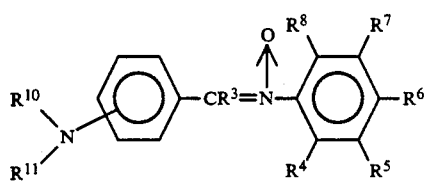

wherein $R^3$, $R^4$, $R^5$, $R^6$, $R^7$, $R^8$, $R^{10}$ and $R^{11}$ have, respectively the same meanings as defined in claim 9.

16. A contrast enhanced material according to claim 9, wherein said material is of the formula

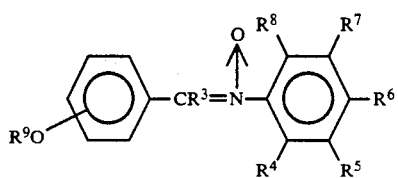

wherein $R^3$, $R^4$, $R^5$, $R^6$, $R^7$, $R^8$, and $R^9$ have, respectively the same meanings as defined in claim 9.

17. A contrast enhanced material according to claim 9, wherein said material is of the formula

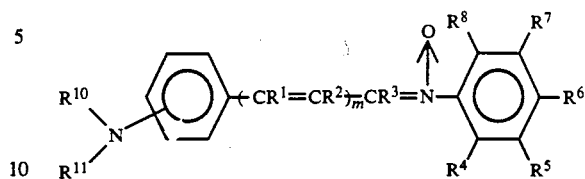

wherein $R^1$, $R^2$, $R^3$, $R^4$, $R^5$, $R^6$, $R^7$, $R^8$, $R^{10}$ and $R^{11}$ have, respectively the same meanings as defined in claim 9 and m is 1 or 2.

18. A contrast enhanced material according to claim 9, wherein said material is of the formula

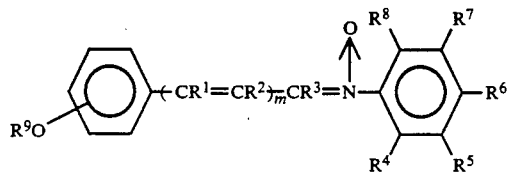

wherein $R^1$, $R^2$, $R^3$, $R^4$, $R^5$, $R^6$, $R^7$, $R^8$, and $R^9$ have, respectively the same meanings as defined in claim 9.

19. An alkali-soluble mixture nitrone compound according to claim 1, wherein $R^4$ to $R^5$ are each independently an alkyl group having 1-8 carbon atoms, a hydrogen atom or a carboxyl group, provided that at least one of $R^4$ to $R^8$ is a carboxy group, and $R^9$, $R^{10}$ and $R^{11}$ are each independently an alkyl group having 1-8 carbon atoms, or a hydrogen atom.

* * * * *